United States Patent [19]

Dietsche

[11] 4,001,215

[45] Jan. 4, 1977

[54] 1,2,5,8-TETRAHYDRO-2,4,6,8-TETRAMETHYL-1,5-DIAZOCINE-2,8-DIOL AND METHOD OF PREPARATION

[75] Inventor: Thomas J. Dietsche, Berkeley, Calif.

[73] Assignee: The Dow Chemical Company, Midland, Mich.

[22] Filed: Mar. 12, 1976

[21] Appl. No.: 666,512

[52] U.S. Cl. .................... 260/239 BC; 71/88; 424/244

[51] Int. Cl.² .................... C07D 245/02

[58] Field of Search .................... 260/239 BC

[56] References Cited

UNITED STATES PATENTS 3,236,837  2/1966  Gaetner .................... 260/239 BC
3,503,939  3/1970  Williams .................... 260/239 BC

FOREIGN PATENTS OR APPLICATIONS 42-4262  2/1967  Japan .................... 260/239 BC

*Primary Examiner*—Donald G. Daus
*Assistant Examiner*—D. B. Springer
*Attorney, Agent, or Firm*—Robert R. Stringham

[57] ABSTRACT

The title compound is readily prepared in good yield by the reaction of acetylacetone with ammonia in methanol. It has fungicidal and insecticidal properties and, by reason of the number and variety of functional groups it contains, should be useful as an intermediate.

7 Claims, No Drawings

1,2,5,8-TETRAHYDRO-2,4,6,8-TETRAMETHYL-1,5-DIAZOCINE-2,8-DIOL AND METHOD OF PREPARATION

BACKGROUND OF THE INVENTION

A. Dornow and H. Machens described (Chem. Berichte 80, pp. 502–5 (1947)) the synthesis of 2,4,6-trimethyl-3-acetylpyridine by warming acetylacetone (2,4-pentane-dione) and ammonium acetate together on a waterbath. These authors suggest the following model for the reaction, in which one molecule of ammonia is condensed with one keto-form dione molecule and one enol-form dione molecule:

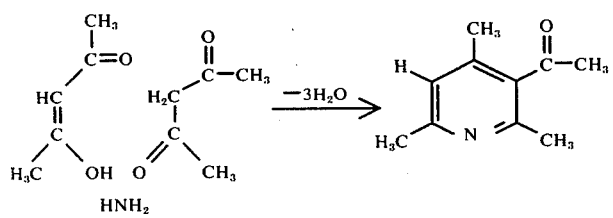

Such a model is consistent with the fact that substantial dissociation of ammonium acetate into ammonia and acetic acid occurs at water (steam) bath temperatures.

A somewhat similar ammonia/diketone condensation reaction was reported (J. Het. Chem., 6, 771–3 (1969)) by E. Campaigne, D. McClure and J. Ashby. In this condensation, both molecules of the diketone apparently reacted in the mol form and the second stage of condensation required for ring closures did not take place:

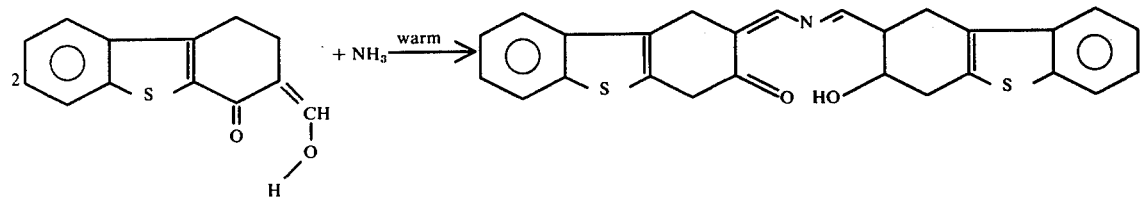

This reaction occurred when either ammonium acetate in acetic acid or gaseous ammonia in ethanol was employed.

Thus, it is surprising that the diazocine compound of the present invention, rather than the trimethyl-acetyl-pyridine, results when acetylacetone is reacted with free ammonia in methanol.

The present inventor has also found that the pyridine compound can be made by heating the subject diazocine in acetic acid. However, the mole ratio of unconverted diazocine to pyridine compound in the resulting reaction mixture is still about 1:3 after 1 hour at about 110°–120° C. Therefore, it is evident that the diazocine is not just a quasi-stable compound and cannot be assumed to have been involved as an intermediate in prior preparations of the pyridine.

A variety of substituted diazocine compounds are known. It is believed that the known compounds most closely related to the compound of the present invention, are as follows:

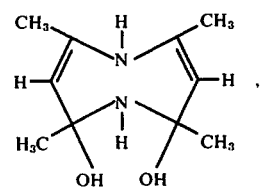

a. Monomers for preparation of polyamides.
U.S.P. 3,503,939.

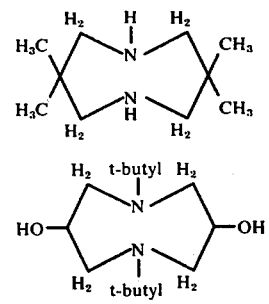

b. Bacteriostats and fungistats.
U.S.P. 3,236,837.

c. Paudler & Zeiler,
J. Org. Chem. 32,
(8) 2425–30 (1967).
Intermediates for preparation of compounds of undisclosed utility.

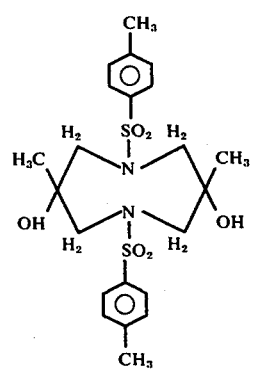

OBJECTS OF THE INVENTION

A principal object of the present invention is to provide a highly novel compound, containing three different types of functional groups, which may be utilized as an intermediate in the preparation of polymers, drugs and pesticides.

A corrolary object is to provide such a compound which may readily be prepared in good yield from a relatively inexpensive principal starting material.

A further object is to provide a novel type of insecticidally active organic compound which does not include such difficultly biodegradable moieties as halogen bonded to carbon.

Another object is to provide a simple, direct method for the preparation of the diazocine compound of the invention.

Still other objects will be apparent to those skilled in the art.

SUMMARY OF THE INVENTION

The present invention is the compound 1,2,5,8-tetrahydro-2,4,6,8-tetramethyl-1,5-diazocine-2,8-diol and the method of preparing it which comprises reacting 2,4-pentane-dione with ammonia as components of a solution in a $C_1$ to $C_3$ alcohol, said reaction being carried out at a temperature such that said solution is a liquid but below about 125° C.

Preferably, the reaction is effected by introducing at least 1 molecular proportion of ammonia for each molecular proportion of the dione in the solution and the contact time is at least 2 hours.

The preferred alcohol is methanol, the preferred reaction temperature range is from about 20° to about 65° C. and the preferred mode of work-up is to strip off the alcohol and distill the crude product, under reduced pressure.

DETAILED DESCRIPTION

The compound of the present invention is obtained as a white solid, which melts at 35°–37° C., by distilling the crude product in a rotary evaporator at 14 mm Hg and collecting the 95°–100° C. overhead cut. It is very soluble in water and is soluble in common organic solvents such as, for example, pentane, alcohols, acetic acid, acetone, dioxane, benzene, chloroform, acetonitrile, carbon disulfide and methylene chloride. It exhibits a tendency to discolor upon prolonged standing at ordinary ambient temperatures and should be stored under nitrogen with refrigeration.

Acetylacetone is manufactured by McKenzie Chemical Works, Inc., Cen. Islip, N.Y. and by Union Carbide, Chemicals and Plastics Division, S. Charleston, W. Va. It tends to discolor and form resins upon prolonged exposure to light and preferably is freshly distilled under reduced pressure before being used to prepare the subject diazocine compound. Acetylacetone is toxic and should be handled with appropriate precautions.

The ammonia employed in the reaction preferably is introduced as the anhydrous gas, by such means as a sparger. In a reaction vessel of generally elongate shape, the gas may be introduced at the bottom at a rate such that adequate stirring results simply from the bubbling action; otherwise a separate stirring means may be employed.

The subject diazocine will form at any reactant ratio such that at least localized contact between the acetylacetone and ammonia in equimolar proportions results. However, it is preferable that contact in these proportions can occur throughout the reaction mixture. That is, the mole ratio of ammonia to acetylacetone introduced to the reaction mixture can be as low as about 1 to 2 but is preferably at least 1 to 1. The only upper limit on this ratio is that imposed by such practical considerations as excessive solvent loss (by entrainment) and handling large volumes of gaseous effluent from the reaction. However, nothing will be gained by the introduction of more ammonia than is required to keep the reaction solution saturated at the reaction pressure employed.

Suitable solvents are lower alcohols, such as methanol, ethanol, n-propanol and isopropanol. Ethanol and methanol, particularly the latter, are preferred. Technical grade alcohols are satisfactory and it does not appear that the presence of water in small amounts is deleterious.

Although the reaction will proceed at temperatures substantially below ordinary ambient temperatures, correspondingly longer contact times will be required to effect a given degree of conversion of the dione. Similarly, although the reaction temperature may be in excess of 65° (the boiling point of methanol at 760 mm), this is not necessary in order to ensure an adequate reaction rate and may tend to favor formation of undesired by-products. Contact times ranging from about 0.25 hour (at a temperature of 125°) to about 24 hours (at 10°) will generally be appropriate.

It is preferred to carry out the reaction at ordinary atmospheric pressures but sub- to superatmospheric pressures may be employed. For example, if temperatures above the boiling point of the reaction solution are to be maintained, a pressure at least equal to the autogenous pressure exerted by the solution will be required.

Any method of introduction which results in contacting of the dione and the ammonia as components of a solution in the alcohol may be employed. Preferably, the ammonia is bubbled into a pre-formed solution of the dione in the alcohol. However, a saturated solution of ammonia in the same or a different $C_1$-$C_3$ alcohol may be used in place of gaseous ammonia and the dione solution may be added to the ammonia solution, rather than vice versa.

The following examples are for purposes of illustration and are not to be construed as limiting the scope of the present invention.

EXAMPLES

1. Preparation of the Diazocine Compound

Anhydrous ammonia was bubbled into a solution of 100 grams (1 mole) of 2,4-pentane dione (Aldrich, P775-4, 99+%) dissolved in 300 ml. of methanol (tech). The temperature rose from room temperature to 60° spontaneously during the first half hour and a yellow color developed. After a total of 2.5 hours, the temperature had subsided to 40° and ammonia introduction was terminated. The reaction mixture was allowed to stir overnight at ambient temperature. The methanol (and water formed by the reaction) was removed under reduced pressure in a rotoevaporator and the residue distilled at 14 mm Hg. The overhead (br 95°–100°) was collected in the amount of 90 g. as a colorless liquid which subsequently solidified. The melting range of the solid was 30°–35°. After being recrystallized from pentane, the solid melted at 35°–37°.

Elemental analysis gave the following results:

|  | C | H | N | O |
|---|---|---|---|---|
| Found | 59.33 | 8.90 | 13.77 | — |

-continued

| | C | H | N | O |
|---|---|---|---|---|
| Calc. C$_{10}$H$_{18}$N$_2$O$_2$ (198.3) | 60.56 | 9.17 | 14.13 | 16.4 |

Infrared and nuclear magnetic resonance (nmr) spectroscopic examinations confirmed the cyclic diazocine structure given above. No pyridine compound was found present.

2. Conversion to 2,4,6-Trimethyl-3-acetylpyridine

Five grams of the product of the preceding example was dissolved in 10 ml of glacial acetic acid and heated at 110°–120° C. for about 1 hour. The solution was stirred with 50% aq. NaOH in amount sufficient to neutralize the acetic acid and the resulting mixture extracted with methylene chloride. The extract was dried and stripped in a rotoevaporator. About 5 grams of a residual product were obtained which, by nmr, consisted of 20–25 wt. % of the unconverted diazocine and 75–80% of 2,4,6-trimethyl-3-acetylpyridine.

3. Biological Testing a. The diazocine compound of Example 1 was tested as a plant-systemic insecticide against Two-spotted Spider Mites and found to give 100% control (kill) of mites feeding for 3 to 6 days on a test plant rooted in vermiculite in which a 100 ppm solution of the compound had been injected. For comparison, the LD$_{95}$ for Kelthane in the same test is 600 ppm. A sufficiently large population of mites is used in this test to permit statistically significant comparisons as to mortality rates with control populations feeding on essentially identical plants and not exposed to the test chemical in any way.

b. The diazocine of Example 1 was applied, at a concentration of 400 ppm, to the root zone (by injection) and to the exposed parts (by immersion) of a bean plant grown in a pot. After the chemical had dried, a ventilated insect cage containing Beet Army Worm larvae was clamped on a leaf. A mortality count made after 7 days showed 100% control (kill) of the larvae had resulted.

c. The diazocine of Example 1 was applied, at a concentration of 400 ppm, to the exposed parts of plants innoculated with Apple Scab fungus (*Venturia inaequalis*) and maintained under conditions of humidity and temperature favorable to infection. Identical innoculated, but untreated, plants were maintained under the same conditions until symptoms of infection were well developed and a comparison was then made. Symptoms development on the treated plants was only about 8% indicating the percent control of the fungus obtained was 92%.

d. A 400 ppm solution of the diazocine was sprayed on the exposed parts of suitable host plants and drenched onto the vermiculite in which the plants were rooted. The plants (and otherwise identical, untreated check plants) were subsequently innoculated with the fungus, Apple Powdery Mildew (*Erysiphe polygoni*) and kept under temperature and humidity conditions conducive to disease growth. After disease symptoms were well developed on the untreated plants, the percent control on the treated plants, by comparison, was found to be about 90%.

What is claimed is:

1. 1,2,5,8-Tetrahydro-2,4,6,8-tetramethyl-1,5-diazocine-2,8-diol.

2. The process of preparing the compound of claim 1 which comprises the step of reacting 2,4-pentanedione with ammonia by contacting said dione with the ammonia as components of a solution in a C$_1$ to C$_3$ alcohol, at a temperature such that said solution is a liquid, but below about 125° C.

3. The process of claim 2 in which said alcohol is methanol.

4. The process of claim 2 in which the temperature is from about 20° to about 65° C.

5. The process of claim 2 in which at least 1 molecular proportion of gaseous ammonia is bubbled into said solution for each molecular proportion of said dione present therein.

6. The process of claim 5 in which the alcohol is methanol and the temperature is from about 20° to about 65°.

7. The process of claim 6 in which said contacting is continued for at least 2 hours.

* * * * *